ary, or Firm—Sidney W. Millard

United States Patent [19]
Webb et al.

[11] Patent Number: 4,937,185
[45] Date of Patent: Jun. 26, 1990

[54] DETECTION OF CIRCULATING ANTIBODIES TO A CANCER MARKER PROTEIN

[75] Inventors: Thomas E. Webb, Columbus, Ohio; Margaret Hanausek-Walaszek, Smithville, Tex.; Frank Mercurio, La Jolla, Calif.

[73] Assignee: The Ohio State University Research Foundation, Columbus, Ohio

[21] Appl. No.: 79,870

[22] Filed: Jul. 31, 1987

[51] Int. Cl.$^5$ .................. G01N 33/53; G01N 33/564; G01N 33/531; C07K 15/00

[52] U.S. Cl. .......................................... 435/7; 436/64; 436/506; 436/543; 436/813; 436/825; 530/352

[58] Field of Search ................. 435/7; 436/503, 505, 506, 518, 543, 547, 808, 813, 819, 545, 579; 530/352

[56] References Cited

U.S. PATENT DOCUMENTS

| | | | |
|---|---|---|---|
| 4,342,566 | 8/1982 | Theofilopoulos et al. | 436/507 |
| 4,594,319 | 6/1986 | Sharma | 436/519 |
| 4,743,678 | 5/1988 | Essex et al. | 436/813 |

FOREIGN PATENT DOCUMENTS

| | | | |
|---|---|---|---|
| 8000026 | 1/1980 | World Int. Prop. O. | 436/506 |
| 0002467 | 6/1985 | World Int. Prop. O. | |
| 8702781 | 5/1987 | World Int. Prop. O. | 436/519 |

OTHER PUBLICATIONS

Lee et al., Breast Cancer Research and Treatment, vol. 6, 1985, pp. 57–65.
Hanausek-Walaszek et al., Biochemical and Biophysical Research Communications, vol. 127, No. 3, 1985, pp. 779–785.
Reeves et al., Proc. Natl. Acad. Sci. USA, vol. 83, Dec. 1986, pp. 9507–9511.

*Primary Examiner*—Esther M. Kepplinger
*Assistant Examiner*—Florina B. Hoffer
*Attorney, Agent, or Firm*—Sidney W. Millard

[57] ABSTRACT

A method and kit are described for detecting the presence of cancers and pre-neoplastic cells that produce an oncofetal phosphoprotein having a molecular weight of approximately 60,000 and having the capacity to increase the release of ribonucleic acid from cell nuclei. The method involves detecting the presence of auto-antibodies to this oncofetal phosphoprotein in a subject suspected of suffering from a cancer or pre-neoplastic cells which produce this cancer marker protein. The kit includes purified oncofetal phosphoprotein.

6 Claims, 2 Drawing Sheets

DETECTION OF CIRCULATING ANTIBODIES TO A CANCER MARKER PROTEIN

This invention was made with Government support under Grants No. 5 RO CA30627-03 and 5 RO1 CA38125-02 awarded by the National Cancer Institute. The Government may have certain rights in the invention.

BACKGROUND OF THE INVENTION

The blood and tissues of animals suffering from a wide variety of cancers contain an oncofetal phosphoprotein (hereinafter referred to as 'cancer marker protein') having a molecular weight of approximately 60,000 and having the capacity to increase the release of ribonucleic acid (RNA) from cell nuclei. See PCT/US84/01932, Publication W085/02467, the disclosure of which is hereby incorporated by reference.

SUMMARY OF THE INVENTION

Cancer marker protein is believed to be produced by cancer cells and pre-neoplastic cells and is found in tissues or circulating in the bloodstream of a subject.

It has been discovered that subjects suffering from cancer and pre-neoplastic cells will frequently produce not only cancer marker protein, but surprisingly, will also produce auto-antibodies specific to the cancer marker protein. Generally, auto-antibodies are naturally occurring antibodies directed against an antigen which the immune system recognizes as foreign, but is in fact an antigen that originates from the organism itself.

Testing for the presence of cancer marker protein is a sensitive method to detect a wide variety of cancers in humans and other mammals. Furthermore, cancer marker protein is present at early stages of the carcinogenic process. Thus, testing for the presence of autoantibodies to cancer marker protein in a sample is useful to detect the presence of cancers, pre-neoplastic cells, and cancer marker protein. Furthermore, testing for the presence of auto-antibodies directed to cancer marker protein in a sample is relatively inexpensive and simple, as compared to other methods of detecting the presence of cancer marker protein.

Cancers and pre-neoplastic cells which produce cancer marker protein can be detected by detecting the presence of auto-antibodies to cancer marker protein in samples obtained from subjects suspected of suffering from such cancer or pre-neoplastic cells. Thus, in this sense, methods of the present invention are indirect. That is, samples are tested for the presence of autoantibodies, i.e., naturally occurring antibodies, specific to cancer marker protein. The presence of autoantibody specific to cancer marker protein is indicative of the presence of cancer marker protein itself which, in turn, is indicative of the presence of cancer and preneoplastic cells.

The formation of an auto-antibody/antigen complex formed of cancer marker protein immunologically reacted with auto-antibodies of the sample indicates that autoantibodies directed to cancer marker protein are present. Cancer marker protein is used as the antigen that is contacted and incubated with a sample obtained from a subject to determine if auto-antibodies specific to cancer marker protein are present in the sample.

This invention also provides a kit to detect the presence of auto-antibodies to cancer marker protein in blood or tissue samples obtained from a subject. The kit contains purified cancer marker protein and instructions on how to contact and incubate the cancer marker protein with a sample from a subject, as well as how to interpret the results of the contact.

This invention includes within its scope the detection of any auto-antibodies to the cancer marker protein present in the subject, e.g., whether freely circulating or already complexed to cancer marker protein.

DETAILED DESCRIPTION OF THE INVENTION

Figure 1:
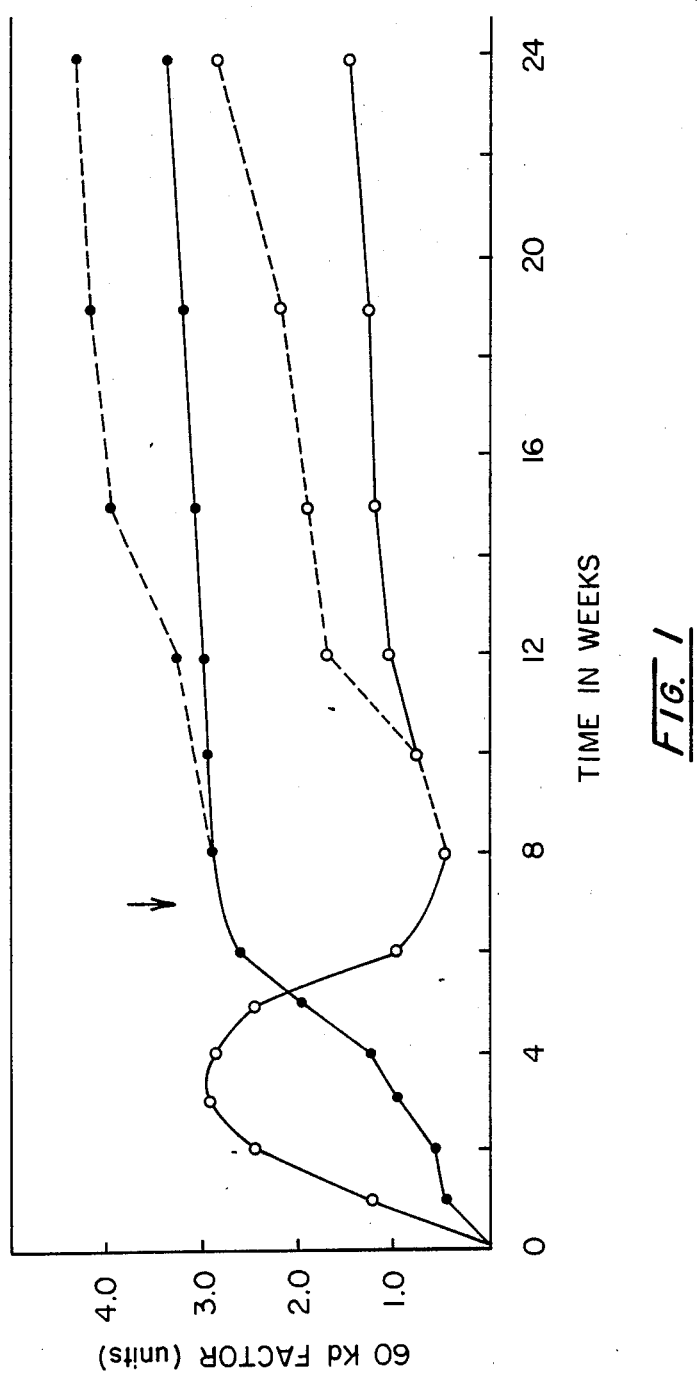
FIG. 1 is a graph showing the kinetic behavior of cancer marker protein in the blood plasma and in liver cytosol of rats over a 24 week period of time postcarcinogen treatment. The curve defined by the shaded points represents the data corresponding to the blood plasma and the curve defined by the open points show liver cytosol values.

In a first aspect this invention is directed to a method of detecting cancer in a subject suspected of suffering from a cancer which produces cancer marker protein by contacting and incubating a sample obtained from the subject with purified cancer marker protein and, determining the presence or absence of a complex formed of cancer marker protein immunologically reacted with auto-antibodies of the sample directed to cancer marker protein, whereby the presence of a complex is indicative of the presence of cancer.

In a second aspect this invention is directed to a method of detecting the presence of pre-neoplastic cells in a subject suspected of having pre-neoplastic cells which produce cancer marker protein by contacting and incubating a sample obtained from the subject with purified cancer marker protein and, determining the presence or absence of a complex formed of cancer marker protein immunologically reacted with autoantibodies of the sample directed to cancer marker protein, whereby the presence of such a complex is indicative of the presence of pre-neoplastic cells.

In a third aspect, the invention is directed to a method of detecting cancer marker protein in a sample obtained from a subject suspected of suffering from a cancer which produces cancer marker protein by contacting and incubating a sample obtained from the subject with purified cancer marker protein and, determining the presence or absence of a complex formed of cancer marker protein immunologically reacted with autoantibodies of the sample directed to cancer marker protein, whereby the presence of a complex is indicative of the presence of cancer marker protein.

In a fourth aspect, the invention is directed to a kit for detecting the presence of auto-antibodies to cancer marker protein in a sample obtained from a subject suspected of suffering from a cancer which produces cancer marker protein having purified cancer marker protein and directions for contacting purified cancer marker protein with a sample, and for determining the presence or absence of a complex formed of cancer marker protein immunologically reacted with autoantibodies in a sample directed to said cancer marker protein, whereby the presence of a complex is indicative of the presence of auto-antibodies to cancer marker protein.

Samples useful in the present invention can be obtained from any appropriate source of auto-antibody in the subject, including, for example, any tissue or blood sample in which such antibodies are present. Interfering proteins and factors must be removed from the sample before testing. Blood samples provide a ready and relatively non-intrusive source of the antibodies and therefore blood samples are preferred. The blood sample is preferably in the form of either plasma or serum as opposed to whole blood. Blood serum is the most preferred blood sample, as all clotting proteins are removed.

A preferred method of the invention uses purified cancer marker protein to detect the presence of auto-antibodies as follows: A sample from the subject, such as blood plasma, is contacted with purified cancer marker protein and incubated, i.e., allowed to remain in contact for a time and under conditions sufficient to allow the cancer marker protein antigen provided to immunologically react with auto-antibodies in the sample. The presence of a resultant auto-antibody/antigen complex is then determined. If such a complex forms, it indicates that the cancer marker protein is or had been present in the mammal. The presence of the cancer marker protein, in turn, indicates that pre-neoplastic cells or neoplastically transformed cells i.e., cancer cells, are actively dividing. The purified cancer marker protein used in the present method desirably has an RNA-releasing activity of at least 10 units, preferably at least 20 units, and most preferably at least 30 units, per milligram of total protein.

The detection of the auto-antibody/antigen complex can be carried out by various techniques, such as radio-immunoassay (RIA). Preferred techniques are the enzyme-linked immunosorbant assay (ELISA) and Western blot methods.

Auto-antibodies to cancer marker protein can also be detected even if they exist as immune complexes in the blood, i.e., already complexed to cancer marker protein. A variety of techniques exist to detect complexed antibodies, e.g., disassociating the complexes and detecting the freed antibodies; or detecting the intact complexes by the use methods such as complement (C1q) binding assays, or polyethylene glycol precipitation tests as described, e.g., in *Immunology*, Section 21.9, Roitt et al., ed. (1985, C. V. Mosby Co.) and references cited therein. Generally, however, such techniques are more laborious than detecting freely circulating antibodies, and hence are not preferred.

Since the method of the present invention detects auto-antibodies to cancer marker protein rather than the cancer marker protein itself, the method is likely to be less dependent on the actual presence of cancer marker protein, i.e., circulating antibodies may be detected even in situations where the cancer marker protein had only previously been present, or at least detectable, e.g., biochemically.

Similarly, the method is not likely to be dependent on the actual presence of cancer cells in the body, for example, it is likely that auto-antibodies to cancer marker protein would likely still be detectable for some time after surgical removal of the tumor itself. The method of this invention could nevertheless still be useful however, e.g., to monitor the decrease in concentration of auto-antibodies as a method of measuring the effectiveness of tumor removal, or as a method of detecting the presence of other tumor foci.

The term "purified cancer marker protein" as used herein refers to cancer marker protein in a form suitable to immunologically react in a detectable fashion with auto-antibodies directed to cancer marker protein. Preferably, purified cancer marker protein exhibits RNA-releasing activity of at least about 10 units per mg total protein. More preferably, purified cancer marker protein exhibits an RNA-releasing activity of greater than about 20 units per mg total protein, and particularly preferred is activity of greater than about 30 units per mg total protein. The purified cancer marker protein is preferably used in its native protein state, i.e., in a state in which it retains its immunological activity with antibodies.

The purified cancer marker protein may be obtained by any suitable method. For example, it may be purified from the blood plasma of cancer patients, produced through genetic engineering techniques, or harvested from cancer cells grown in tissue culture medium by usual techniques. If obtained from tissue culture medium, it is preferred that little or no exogenous protein be added to the culture.

The purified cancer marker protein preferably has the following characteristics:

(a) soluble in a 30% saturated aqueous ammonium sulfate solution at a temperature of 5° C.;
(b) molecular weight of approximately 60,000;
(c) capable of being precipitated from an aqueous solution by 3.3% streptomycin sulfate;
(d) substantially no autophosphorylation activity but is capable of being phosphorylated with adenosine triphosphate in the presence of an exogenous protein kinase;
(e) substantially no protein kinase activity;
(f) capable of the liberation of ribonucleic acid from cell nuclei;
(g) substantially free of albumin;
(h) normally absent from the maternal blood of noncancerous normal pregnant mammals of the species in which said protein is being determined; and
(i) a pI value of approximately 5.2.

The concentration of cancer marker protein circulating in the blood varies markedly over time. Variation in blood plasma and in liver cytosol concentrations are shown in FIG. 1 in which it can be seen that the concentration of cancer marker protein in the serum of a carcinogen-treated rat rose sharply over the first three weeks post-carcinogen treatment followed by a decrease almost as sharply over the next 5 weeks. The humoral response to the oncofetal protein seen in rats is consistent with the finding that the rat's immune system has not been previously exposed to this antigen. The concentration of the protein in rat liver cytosol slowly increased and then plateaued at a maximum level.

Figure 2:
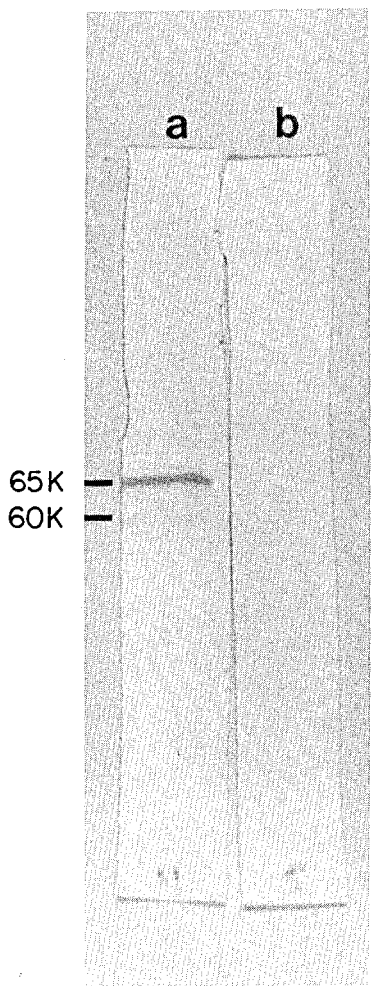
FIG. 2 is a Western blot showing the results of contacting and incubating purified cancer marker protein with antisera from a subject suffering from cancer (shown in column "a") and the results of contacting and incubating serum from a healthy subject with purified cancer marker protein (shown in column "b").

Western blot analysis demonstrates the presence of circulating auto-antibodies specific to cancer marker protein. Such a Western blot is shown in FIG. 2. After separation according to molecular weight in an SDS-polyacrylamide gel and electrophoretic transfer of the proteins to nitrocelluose paper, the electro-blot was incubated first with anti-sera from either (a) rat 40 days post-carcinogen treatment, or (b) normal control rat, then with second antibody-horseradish peroxidase conjugate and appropriate chromogenic substrate.

FIG. 2 also shows the presence of two proteins. One is the 60 kd cancer marker protein. The other, a larger 65 kd protein, is believed to be a precursor of the smaller cancer marker protein. The auto-antibodies corresponding to these proteins are generally cross-reactive and are not present in the healthy control subject.

RNA-releasing activity can be determined by techniques well known to those skilled in the art. Particularly preferred is to determine RNA-releasing activity by the following procedure.

Male Sprague-Dawley rats weighing approximately 250 grams are fasted for 18 hours. For the preparation of cytosol, the rat livers are dissected out, homogenized in a volume of 0.25 M sucrose-TMK buffer which is twice the wet weight (milliliters/gram) of the livers.

The TMK buffer used has the following composition:
50 mM Tris(hydroxymethylamino) methane hydrochloride
25 mM potassium chloride
2.5 mM magnesium chloride
This buffer has a pH of 7.5.

The homogenate is centrifuged at 100,000 g for 90 minutes and the supernatant removed and dialyzed overnight against TMK buffer.

For the preparation of nuclei, rats are injected with 50 micro curies of [6-$^{14}$C]orotic acid (specific activity 323 micro curies/milligram, available from New England Nuclear Corporation, Boston, Mass.) as described in Cancer Res., 33:1821-1828 (1973), the disclosure of which is hereby incorporated by reference. After allowing 30 minutes for prelabelling, the rat livers are dissected out, homogenized in a volume of 2.3 M sucrose/3.3 mM calcium acetate aqueous solution which is 15 times the weight of the liver. This homogenate is centrifuged at 34,000 g for 60 minutes at 4° C. The nuclear pellet is washed with a solution containing 1 M sucrose/1 mM calcium acetate and resuspended in the same solution.

The cytosol remaining after the overnight dialysis step is then used to prepare a cell-free system containing $5 \times 10^6$ prelabeled nuclei per milliliter of medium, 5 milligrams of dialyzed cytosol protein per milliliter and having the following additional components:
30 mM Tris-HCl (pH 7.5)
25 mM potassium chloride
2.5 mM magnesium chloride
0.5 mM calcium chloride
0.3 mM manganese chloride
5.0 mM sodium chloride
2.5 mM phosphoenol pyruvate
35 units/milliliter of pyruvate kinase
2.5 mM sodium dihydrogen phosphate
5.0 mM spermidine
2.0 mM dithiothreitol
2.0 mM adenosine triphosphate
300 microgram/milliliter of low molecular weight yeast RNA. Up to 100 microliters of plasma or 200 microliters of a column fraction containing the cancer marker protein are added per 1 milliliter of the cell-free medium and incubated at 30° C. for 30 minutes. The nuclei are removed by centrifugation at approximately 500-1,000 g, the resulting supernatant liquor separated and the RNA and protein precipitated therefrom with a 5% aqueous solution of trichloroacetic acid. The resultant precipitate is washed in ethanol, dissolved in solubilizer and counted in liquid scintillant. The preferred solubilizer is "Unisol" and the preferred scintillant "Unisol Complement", both available from Isolab, Inc., Akron, Ohio. A control is treated in the same manner, except of course, that none of the specimen being tested is added thereto. One unit of RNA-releasing activity represents an increase in the count of 1% of the total nuclear counts and, for obvious reasons, results are normally expressed as units of activity per milligram of protein added to the test material.

Although the characteristics already specified are believed to define the instant cancer marker protein uniquely, it should be noted that various other properties of cancer marker protein have been observed and further characterize this protein. The cancer marker protein is fairly stable, retaining full biochemical activity (i.e., RNA-releasing activity) and showing little or no change in size during storage in plasma at -20° C. for at least three years. However, the protein is heat-labile, being completely destroyed by heating to 65° C. for 10 minutes. The protein has little or no single strand ribonuclease activity, and electrophoresis on sodium dodecylsulfate-polyacrylamide gel suggests that it consists of a single polypeptide chain, since a single band appears in the 60,000 molecular weight region.

Cancer marker protein preparations have been isolated from both humans and other mammals, and the protein preparations from different species appear to be generally similar in molecular weight and other chemical properties. However, the cancer marker proteins from different species are not believed to be immunologically equivalent, e.g., an antibody to the rat cancer marker protein does not generally cross-react with human cancer marker protein. When the purified cancer marker protein preparation is to be used for the production of antibodies, as described below, or for the purpose of detection of auto-antibodies, it is particularly preferable to begin the preparation process with a sample from the species with which the method is to be used.

The following process describes a preferred method of preparing the instant cancer marker protein by purification from the blood serum of a cancer subject.

The first step involves the separation of the fraction of serum protein which is not precipitated by 30% saturated aqueous ammonium sulfate solution from the serum of a mammal suffering from cancer. Since the purpose of the ammonium sulfate precipitation step is to remove low molecular weight material, the whole fraction which precipitates between 30% and 100% saturation may be used in further purification. However, in generally, it is preferred to use the fraction precipitating between 30% and 60% saturation. Such a fraction contains substantially all of the cancer marker protein.

The second step of the instant purification process involves dialysis, desirably conducted at a pH in the range of about 7 to about 8. In a particularly preferred embodiment of the invention, the dialysis is conducted by dispersing the serum protein fraction in a tris(hydroxymethylamino)methane/potassium chloride/magnesium chloride buffer having a pH of about 7.5 and dialyzing the resultant protein solution against the same buffer. Overnight dialysis normally provides sufficient purification in this step of the instant process.

In the third step of the instant purification process, the fraction of the protein having a molecular weight of about 60,000 is separated. Although, as already noted, the molecular weight of the cancer marker protein and its precursor are both about 60,000, the fractions eluting in the molecular weight range of 55,000 to 70,000 should usually be collected to ensure reasonably complete recovery of the cancer marker protein. This separation can be achieved by centrifugation, but it is preferred that this separation be effected by chromatography of the dialyzed cancer marker protein from the second step of the instant process on a molecular sieve solid phase. Those skilled in the art will be aware of a variety of molecular sieve materials which can be used for this purpose; the preferred molecular sieve material is the cross-linked hydrophobic agarose resin available commercially from a variety of sources under the trade name Sepharose CL-6B. The liquid phase in the chromatography process is preferably the same TMK buffer used in the aforementioned preferred embodiment of the dialysis step. However, following the chromatography step, the purified cancer marker protein is still contaminated by a considerable amount of serum albumin (molecular weight about 68,000).

It is preferred that the purified cancer marker protein to be contacted with the sample be "substantially free" of albumin sinoe albumin has a similar molecular weight to the cancer-marker protein and would probably interfere with the detection of auto-antibodies to cancer marker protein. The term "substantially free" as used herein refers to a concentration of albumin that does not preclude the use of the purified cancer marker protein in the method of this invention.

It is therefore preferred that the instant purification process includes the step of treating the protein fraction obtained from the third step to remove albumin therefrom. The preferred method for removal of albumin without causing any deleterious effects to the cancer marker protein itself is chromatography on a solid medium capable of absorbing albumin, and a preferred medium for this purpose is that available commercially under the trade name CM Affi-Gel Blue (obtainable from Bio-Rad Lab., Richmond, Calif.).

Further processing to permit the cancer marker protein to be isolated in even higher purity involves such procedures as affinity chromatography on single stranded DNA cellulose (Sigma Chem. Co., St. Louis, Mo.).

It should be noted that once purified cancer marker protein has been prepared, the purification of later batches of cancer marker protein can be enhanced by treating the purified cancer marker protein isolated from the molecular sieve chromatography step (before or after removal of albumin therefrom) with known antibody-containing serum, e.g., obtained from a mouse immunized with purified cancer marker protein. As those skilled in the art are aware, this treatment will cause precipitation of a cancer marker protein/antibody complex which can then be separated, for example by centrifugation, and broken down by methods familiar to those skilled in the art to Yield the purified cancer marker protein and the antibody; for example the protein/antibody complex may be broken down on a column of protein A agarose (sold by BRL, Gaithersburg, Md.; directions for use of this material are supplied by the manufacturer). The purified protein fraction can then be used as called for in the instant invention.

Kits of the present invention include purified cancer marker protein as well as directions for contacting and incubating the cancer marker protein with a sample for determining the presence of an auto-antibody/antigen complex. These directions are such that the user of the kit will understand the likelihood that the presence of such a complex is a positive indication of the presence of cancer marker protein in the subject tested, and in turn, of cancer or pre-neoplastic cells. These directions could be located on the package form utilized for the cancer marker protein or in a separate insert in a container, such as a box, housing the kit.

EXAMPLE 1

This example illustrates a process for purification of the cancer marker protein.

Plasma obtained from ten human patients having cancers at eight different sites was pooled, then fractionated with ammonium sulfate. The protein fraction precipitating between 30 and 50% saturation of the aqueous ammonium sulfate solution, which fraction was found to contain all the RNA-releasing activity, was dissolved in approximately 5 ml of the aforementioned TMK buffer, then dialyzed overnight against the same buffer. An aliquot of the dialyzed solution containing approximately 150 mg of total protein was applied to a 1.5 ×90 cm column of the molecular sieve resin, Sepharose CL-6B. The column was eluted with the aforementioned TMK buffer and 3 ml fractions were collected.

Further purification of the fractions eluting from the molecular sieve column at a molecular weight of 55,000–70,000 was effected by a further chromatography on a 1.0×10.0 cm column of CM Affi-Gel Blue, in order to remove albumin from the purified cancer marker protein. A sample containing 25.0 mg of protein was suspended in the aforementioned TMK buffer, loaded onto the column and eluted with 0.4 M potassium chloride-TMK buffer. Dialysis of eluate and electrophoresis on sodium dodecylsulfate-polyacrylamide gel confirmed that this treatment substantially completely removed albumin from the purified cancer marker protein preparation. The electrophoretograms produced only a single band corresponding to the cancer marker protein, suggesting that this protein is composed of a single polypeptide chain.

Further purification can be accomplished by the following affinity chromatography technique. The DNA column (3.5×9.0 cm) (D-8273, Sigma Chemical Co., St. Louis, Mo.) was equilibrated with 50 mM NaCl-TMK equilibrating buffer (TMK =50 mM Tris-HCl, pH 7.5-25 mM KCl-2.5 mM $MgCl_2$) and the active protein fractions from the CM Affi-Gel Blue column were applied in equilibrating buffer containing 1.0 mM dithiothreitol. After recycling the sample through the column twice, the column was washed with 50 mM NaCl-TMK buffer, then the oncofetal RNA transport factor was eluted with 2.0 M NaCl-TMK buffer. The eluted factor was concentrated and dialyzed against TMK buffer in an ultrafiltration cell (Biomolecular Dynamics, Beaverton, Or.).

EXAMPLE 2

This example illustrates a procedure for contacting, incubating and detecting the presence of an auto-antibody/antigen complex between purified cancer marker protein and circulating auto-antibodies.

Proteins purified as above are separated according to molecular weight by sodium dodecylsulfate (7% polyacrylamidege gel electrophoresis), then electrophoretically transferred to nitrocellulose paper using a Transblot apparatus (Bio-Rad Labs, Richmond, Calif.). Following transfer in 25 mM Tris-192 mM glycine -20% (v/v) methanol for 2 h at 250 mA, the blots are incubated in Blotto buffer (composed of 5% Carnation nonfat dry milk, 0.2 M NaCl, 0.05 M sodium phosphate, pH 7.5,) for 2 h at 25° C. The blots are then transferred to fresh Blotto buffer containing a 1:10 dilution of the appropriate anti-sera for a further 2 h incubation at 25° C., and overnight at 5° C. After washing three times with Blotto buffer, the blots are incubated with goat anti-rat immunoglobulin G-horseradish peroxidase conjugate (Bio-Rad Labs, Richmond, Calif.) that has been diluted 1:1000 in Blotto buffer for 2 h at 25° C., rinsed twice in phosphate buffered saline 0.05% Tween 20 (Sigma Chem. Co., St. Louis, Mo.), twice in buffered saline only, then developed in fresh developing buffer (2.6 mM 4-chloro-1-naphthol-0.02 M NaCl-0.05 M phosphate - 0.01% $H_2O_2$ - 18% (v/v) methanol, pH 7.5) for 5 to 30 min at 25° C. Development is stopped by Immersing the blot in double distilled water and the blot is viewed for evidence of the presence of an immunological reaction. (See, FIG. 2). All incubations are conducted with gentle rocking.

It will be apparent to those skilled in the art that numerous changes and modifications can be made in the preferred embodiments of the invention described above without departing from the spirit and scope of the invention. Accordingly, the whole of the foregoing description is to be construed in an illustrative rather than a limitative sense, the scope of the invention being defined solely by the appended claims.

What is claimed is:

1. A method of detecting the presence or absence of pre-neoplastic cells in a subject suspected of having pre-neoplastic cells which produce a cancer marker protein, or determining the presence or absence in the blood of a subject of auto-antibodies to a cancer marker protein produced by cancer cells, said cancer marker protein having the characteristics of:
   (i) a molecular weight of approximately 60,000;
   (ii) being capable of being precipitated from an aqueous solution by 3.3% streptomycin sulfate;
   (iii) having substantially no autophosphorylation activity but being capable of being phosphorylated with adenosine triphosphate in the presence of an exogenous protein kinase;
   (iv) having substantially no protein kinase activity;
   (v) being capable of the liberation of ribonucleic acid from cell nuclei;
   (vi) being normally absent from the maternal blood of non-cancerous normal pregnant mammals of the species in which said protein is being determined; and
   (vii) having a pI value of approximately 5.2,
said method comprising the steps of:
   a. contacting and incubating a sample obtained from said subject with a purified form of said cancer marker protein, said purified form of said cancer marker protein having the characteristics of:
      (i) being soluble in a 30% saturated aqueous ammonium sulfate solution at a temperature of 5° C.;
      (ii) having a molecular weight of approximately 60,000;
      (iii) being capable of being precipitated from an aqueous solution by 3.3% streptomycin sulfate;
      (iv) having substantially no autophosphorylation activity but being capable of being phosphorylated with adenosine triphosphate in the presence of an exogenous protein kinase;
      (v) having substantially no protein kinase activity;
      (vi) being capable of the liberating ribonucleic acid from cell nuclei;
      (vii) being substantially free of albumin;
      (viii) being normally absent from the maternal blood of non-cancerous normal pregnant mammals of the species in which said protein is being determined; and
      (ix) having a pI value of approximately 5.2;
   b. determining the presence or absence of a complex formed of said cancer marker protein immunologically reacted with auto-antibodies of said sample directed to said cancer marker protein
whereby the presence of said complex is indicative of the presence of pre-neoplastic cells or of the presence of the auto-antibodies.

2. The method of claim 1 wherein said purified cancer marker protein exhibits an RNA-releasing activity of at least 10 units per milligram of total protein.

3. The method of claim 2 wherein said purified cancer marker protein exhibits an RNA-releasing activity of at least 20 units per milligram of total protein.

4. The method of claim 2 wherein said purified cancer marker protein exhibits an RNA-releasing activity of at least 30 units per milligram of total protein.

5. The method of claim 2 wherein said sample is blood serum or blood plasma.

6. The method of claim 2 wherein said determination is performed using a method selected from the group consisting of Western blot analysis, enzyme linked immunosorbant assay, and radioimmunoassay.

* * * * *